(12) United States Patent
Fujieda et al.

(10) Patent No.: US 7,374,286 B2
(45) Date of Patent: May 20, 2008

(54) OPHTHALMIC APPARATUS AND A METHOD FOR CALCULATING INTERNAL EYE REFRACTIVE POWER DISTRIBUTION

(75) Inventors: Masanao Fujieda, Toyohashi (JP); Yukinobu Ban, Nishio (JP)

(73) Assignee: Nidek Co., Ltd., Gamagori (JP)

( * ) Notice: Subject to any disclaimer, the term of this patent is extended or adjusted under 35 U.S.C. 154(b) by 251 days.

(21) Appl. No.: 11/183,754

(22) Filed: Jul. 19, 2005

(65) Prior Publication Data

US 2006/0028619 A1    Feb. 9, 2006

(30) Foreign Application Priority Data

Jul. 20, 2004  (JP) .............................. 2004-212272

(51) Int. Cl.
*A61B 3/10* (2006.01)

(52) U.S. Cl. ...................... 351/205; 351/212; 351/246

(58) Field of Classification Search ................. 351/205
See application file for complete search history.

(56) References Cited

U.S. PATENT DOCUMENTS

| | | | |
|---|---|---|---|
| 5,432,596 A | 7/1995 | Hayashi | |
| 5,500,697 A | 3/1996 | Fujieda | |
| 5,907,388 A | 5/1999 | Fujieda | |
| 6,033,075 A | 3/2000 | Fujieda et al. | |
| 6,655,805 B2 | 12/2003 | Fujieda | |
| 6,796,653 B2* | 9/2004 | Shirayanagi | ................. 351/159 |
| 7,134,752 B2* | 11/2006 | Perrott et al. | ................ 351/159 |

FOREIGN PATENT DOCUMENTS

| EP | 1 393 700 A1 | 3/2004 |
|---|---|---|
| JP | A 10-108837 | 4/1998 |
| JP | A 11-276437 | 10/1999 |

* cited by examiner

*Primary Examiner*—Jessica T Stultz
(74) *Attorney, Agent, or Firm*—Oliff & Berridge, PLC

(57) ABSTRACT

An ophthalmic apparatus and a method for calculating internal refractive power distribution of an eye of an examinee, which allow easily evaluating refractive power distribution of a crystalline lens, an intraocular lens and the like. The ophthalmic apparatus has a unit which inputs respective measurement data on corneal refractive power distribution and whole refractive power distribution of the eye, the respective distribution referring to a reference axis, and a unit which obtains the internal refractive power distribution of the eye referring to the reference axis based on the inputted respective measurement data, obtains a prism component in the internal refractive power distribution with respect to the reference axis, and obtains internal refractive power distribution of the eye where the prism component is removed.

5 Claims, 7 Drawing Sheets

OPHTHALMIC APPARATUS AND A METHOD FOR CALCULATING INTERNAL EYE REFRACTIVE POWER DISTRIBUTION

BACKGROUND OR THE INVENTION

1. Field of the Invention

The present invention relates to an ophthalmic apparatus for obtaining internal refractive power distribution of an eye, and a method for calculating the same.

2. Description of Related Art

Conventionally, an ophthalmic apparatus has been proposed which obtains internal (intraocular) refractive power distribution of an eye between a corneal posterior surface and a retina based on data on corneal refractive power distribution of the eye obtained by a corneal shape measurement apparatus or the like and data on whole refractive power distribution of the eye obtained by a wave front aberration measurement apparatus or an eye refractive power measurement apparatus, and displays the obtained internal refractive power distribution in a color-scaled map. With the use of this kind of apparatus, refractive power distribution of a crystalline lens, an intraocular lens implanted in the eye, and the like may be estimated. However, in the case of an eye with keratoconus and an eye having its axis deviated (decentered) at the time of corneal refractive surgery, the refractive power distribution of the crystalline lens cannot be estimated accurately since a corneal posterior surface as well as a corneal surface of the eye with keratoconus, and a corneal surface of the eye with the deviated axis are widely distorted, and thereby a prism component (component of tilt) is included in the internal refractive power distribution. Also in the case of an eye where the intraocular lens is implanted in a slanting position, the refractive power distribution of the intraocular lens cannot be estimated accurately since the prism component is included in the internal refractive power distribution.

SUMMARY OF THE INVENTION

An object of the invention is to overcome the problems described above and to provide an ophthalmic apparatus and a method for calculating internal refractive power distribution of an eye, which allow easily evaluating refractive power distribution of a crystalline lens, an intraocular lens and the like.

To achieve the objects and in accordance with the purpose of the present invention, an ophthalmic apparatus has an input unit which inputs respective measurement data on corneal refractive power distribution and whole refractive power distribution of an eye of an examinee, the respective distribution referring to a reference axis, and a calculation unit which obtains internal refractive power distribution of the eye referring to the reference axis based on the inputted respective measurement data, obtains a prism component in the obtained internal refractive power distribution with respect to the reference axis, and obtains internal refractive power distribution of the eye where the obtained prism component is removed.

In another aspect of the invention, a method for calculating internal refractive power distribution of an eye of an examinee include's the steps of inputting respective measurement data on corneal refractive power distribution and whole refractive power distribution of the eye, the respective distribution referring to a reference axis, obtaining internal refractive power distribution of the eye referring to the reference axis based on the inputted respective measurement data, obtaining a prism component in the obtained internal refractive power distribution with respect to the reference axis, and obtaining internal refractive power distribution of the eye where the obtained prism component is removed.

Yet, in another aspect of the invention, a method for calculating internal refractive power distribution of an eye of an examinee includes the steps of inputting respective measurement data on corneal refractive power distribution and whole refractive power distribution of the eye, the respective distribution referring to a reference axis, obtaining internal refractive power distribution of the eye referring to the reference axis based on the inputted respective measurement data, obtaining an axial angle with respect to the reference axis, of a prism component in the obtained internal refractive power distribution, obtaining prism components in respective rings of varying diameters having the reference axis as its center while setting axial angles of the prism components at the same axial angle as the prism component, and obtaining internal refractive power distribution respectively in the rings of the varying diameters, where the prism components are removed.

Additional objects and advantages of the invention are set forth in the description which follows, are obvious from the description, or may be learned by practicing the invention. The objects and advantages of the invention may be realized and attained by the ophthalmic apparatus and the method for calculating the internal refractive power distribution in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
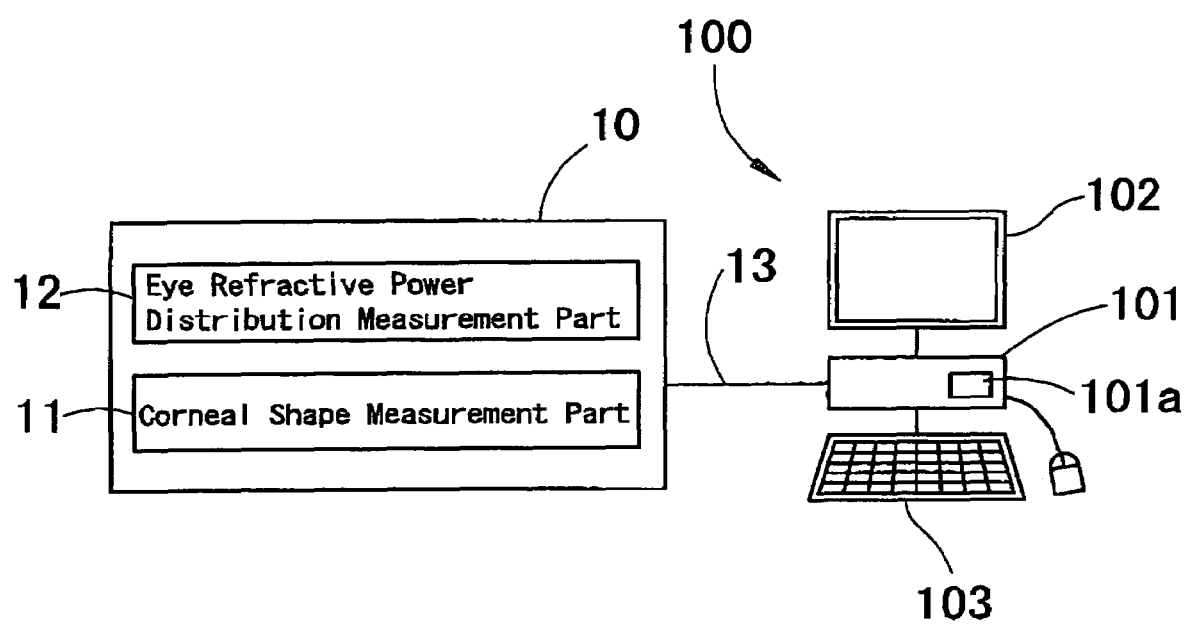
FIG. 1 is a view showing a schematic configuration of an ophthalmic system for obtaining internal refractive power distribution of an eye consistent with the present invention.

A detailed description of one preferred embodiment of an ophthalmic apparatus and a method for calculating internal refractive power distribution of an eye embodied by the present invention is provided below with reference to the accompanying drawings. FIG. 1 is a view showing a schematic configuration of an ophthalmic system for obtaining internal refractive power distribution of an eye. A measurement apparatus 10 includes a corneal shape measurement part 11 and an eye refractive power distribution measurement part 12. Respective measurement data on a corneal shape and eye refractive power distribution obtained by the measurement apparatus 10 is inputted into a computer 100 via a cable 13 or a recording media. The computer 100 includes a processor 101 equipped with a program for obtaining the internal refractive power distribution, a display 102, and an input device 103 such as a keyboard.

Figure 2:
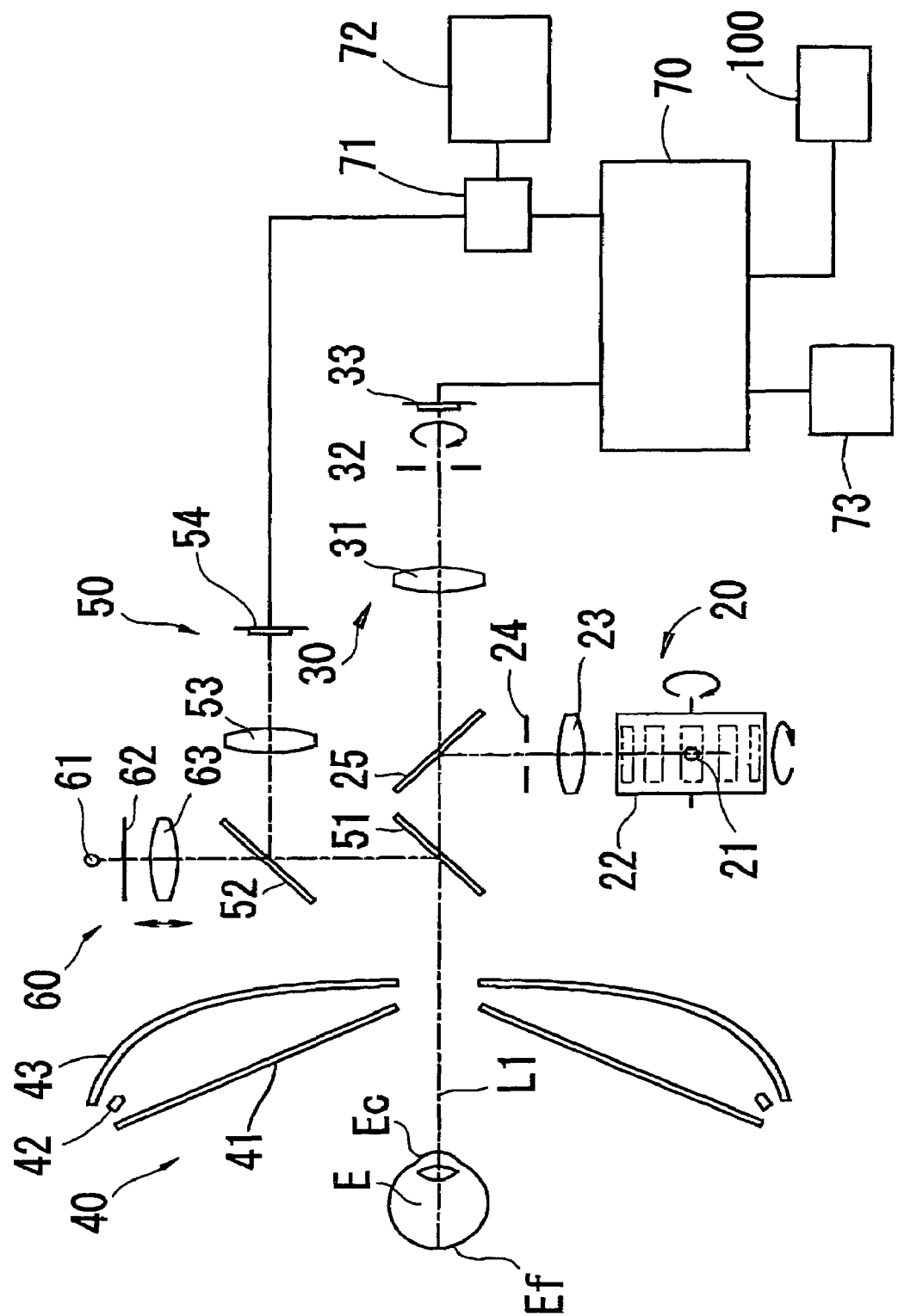
FIG. 2 is a view showing a schematic configuration of an optical system in a measurement apparatus in the ophthalmic system.
Figure 3:
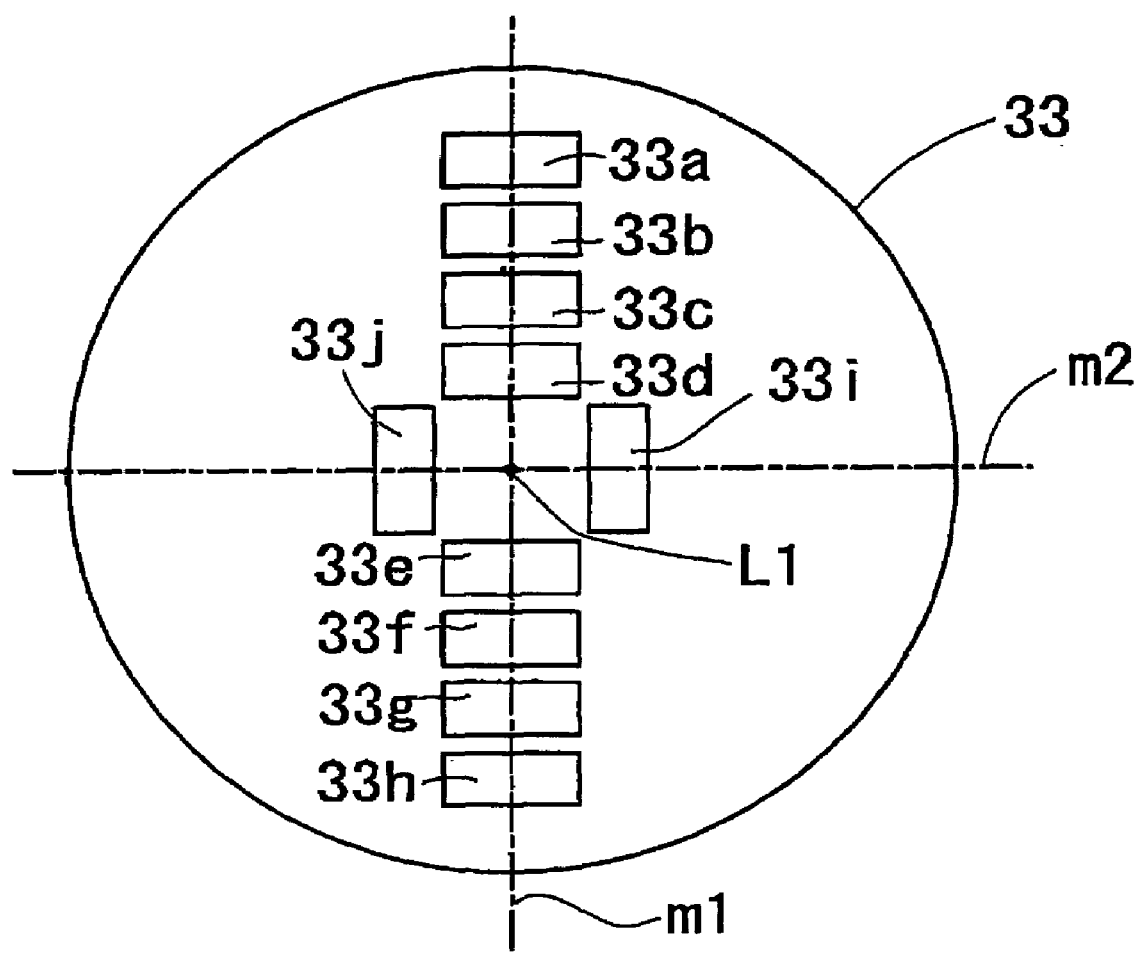
FIG. 3 is a view showing a schematic configuration of photodetectors in an eye refractive power distribution measurement part in the measurement apparatus.

FIG. 2 is a view showing a schematic configuration of an optical system in the measurement apparatus 10. A measurement optical system in the eye refractive power distribution measurement part 12 includes a slit light projection optical system 20 and a photo-receiving optical system 30, having a measurement optical axis L1. The projection optical system 20 includes an infrared light source 21 for measurement, a rotation sector 22 where slits are formed, a projection lens 23, a diaphragm 24 and a beam splitter (half mirror) 25, and projects slit-shaped measurement light onto a fundus Ef of an examinee's eye E by rotation of the rotation sector 22. The photo-receiving optical system 30 includes the beam splitter 25, a photo-receiving lens 31, a diaphragm 32 and a photo-receiving part 33, and photo-receives the measurement light reflected by the fundus Ef. The photo-receiving part 33 is, as shown in FIG. 3, provided with ten photodetectors 33a to 33j arranged in positions approximately conjugate with a cornea Ec of the eye E. Among them, the photodetectors 33a to 33h are placed in a line m1 which intersects with the optical axis L1, and the respective pairs of photodetectors 33a and 33h, the photodetectors 33b and 33g, the photodetectors 33c and 33f, and the photodetectors 33d and 33e are arranged symmetrically with respect to the optical axis L1. Configuration distances between (positions of) these four pairs of photodetectors are set so that refractive power may be obtained at positions varying according to a meridian direction on the cornea Ec. On the other hand, the photodetectors 33i and 33j are placed in a line m2 orthogonal to the line m1, and arranged symmetrically with respect to the optical axis L1. In addition, the rotation sector 22 and the photo-receiving part 33 are respectively rotated about the optical axis L1 in synchronization with each other.

A measurement optical system in the corneal shape measurement part 11 includes a placido-ring image projection optical system 40 and an image-pickup optical system 50, having the measurement optical axis L1. The projection optical system 40 includes a placido plate 41 where a number of ring-shaped targets are formed, an infrared light source 42 which illuminates the placido plate 41 from behind, and a reflecting plate 43. The image-pickup optical system 50 includes a beam splitter (half mirror) 51, a beam splitter (dichroic mirror) 52, a photographing lens 53, and a CCD camera 54 being image-pickup means. The image-pickup optical system 50 doubles as an observation optical system for an anterior segment of the eye E.

An output from the camera 54 is inputted into an image processing part 71 having an image memory. The image processing part 71 is connected to a display 72 and an arithmetic control part 70. An output from the photo-receiving part 33 is inputted into the arithmetic control part 70. The arithmetic control part 70 has a function of calculating the corneal shape and the eye refractive power distribution. An input part 73 has various switches for inputting a command signal into the arithmetic control part 70.

In addition, the measurement apparatus 10 includes respectively rotated about the optical axis L1 in synchronization with each other.

A measurement optical system in the corneal shape measurement part 11 includes a placido-ring image projection optical system 40 and an image-pickup optical system 50, having the measurement optical axis L1. The projection optical system 40 includes a placido plate 41 where a number of ring-shaped targets are formed, an infrared light source 42 which illuminates the placido plate 41 from behind, and a reflecting plate 43. The image-pickup optical system 50 includes a beam splitter (half mirror) 51, a beam splitter (dichroic mirror) 52, a photographing lens 53, and a CCD camera 54 being image-pickup means. The image-pickup optical system 50 doubles as an observation optical system for an anterior segment of the eye E.

An output from the camera 54 is inputted into an image processing part 71 having an image memory. The image processing part 71 is connected to a display 72 and an arithmetic control part 70. An output from the photo-receiving part 33 is inputted into the arithmetic control part 70. The arithmetic control part 70 has a function of calculating the corneal shape and the eye refractive power distribution. An input part 73 has various switches for inputting a command signal into the arithmetic control part 70.

In addition, the measurement apparatus 10 includes a fixation target presenting optical system 60 having the optical axis L1. The fixation target presenting optical system 60 includes a visible light source 61, a fixation target 62 and a lens 63 which is movable in a direction of the optical axis L1. The lens 63 is moved in the optical axis direction to fog the eye E at the time of eye refractive power distribution measurement.

At the time of measurement, an infrared light source for anterior-segment illumination which is unillustrated is lit, and an image of the anterior-segment of the eye E picked up by the camera 54 is displayed on the display 72. In addition, the light source 21 which doubles as a light source for alignment is lit to form a corneal reflex at the center of the cornea Ec as a target for alignment in the up/down and right/left directions, which is displayed on the display 72. An examiner observes the anterior-segment image displayed on the display 72 to perform alignment of the optical system so that the reflex formed by the light source 21 and an unillustrated reticle have a predetermined relationship. Alignment in the back/forth direction (working distance direction) is performed so that the reflex formed by the light source 21 comes into focus (for this alignment, a separate alignment detection system may be provided).

In corneal shape measurement, the light source 42 is lit after the completion of the alignment, and a placido-ring image picked up by the camera 54 is stored in the image memory of the image processing part 71. The image processing part 71 subjects the placido-ring image to image processing to detect an edge thereof. Then, the arithmetic control part 70 controls to obtain corneal curvature distribution every predetermined angle (for example, in steps of one degree) with reference to the corneal center (i.e., the reflex formed by the light source 21).

In the eye refractive power distribution measurement, after the completion of the alignment, the slit-shaped measurement light is projected onto the fundus Ef by the rotation of the rotation sector 22, and the measurement light is reflected by the fundus Ef to be photo-received on the photo-receiving part 33. As for the eye refractive power distribution, it is obtained as follows. The position of the optical axis L1 is obtained from a phase difference between output signals from the photodetectors 33i and 33j, and the refractive power at the corneal positions corresponding to the respective photodetectors in one meridian direction is obtained based on the output signals from the photodetectors 33a to 33h. Then, by rotating the rotation sector 22 and the photo-receiving part 33 respectively about the optical axis L1, for example, in steps of one degree, the arithmetic control part 70 obtains the refractive power distribution which varies according to the meridian direction at each rotational step, (for more details, refer to U.S. Pat. No. 5,907,388 corresponding to Japanese Patent Application Unexamined Publication No. Hei10-108837).

The respective measurement data on the corneal shape and the eye refractive power distribution obtained by the measurement apparatus 10 is inputted into the computer 100 through operation of the input part 73, and stored in a memory part 101a provided to the processor 101. In accordance with an instruction from the input device 103, the processor 101 carries out a program for calculating the internal refractive power distribution to display its calculation result on the display 102. The program for calculating the internal refractive power distribution is previously stored in the memory part 101a.

In general, a corneal shape measurement apparatus and a wavefront aberration measurement apparatus (the eye refractive power distribution measurement apparatus in the present embodiment) respectively incorporate a fixation target (fixation target presenting optical system), on which the examinee's eye is fixated to be measured at the time of measurement. The human eye is an asymmetric optical system, and has various axes such as an optical axis which passes through the curvature center of an optics of an eye, a line of sight which connects the center of an entrance pupil and the fixation target (fixation point), and a visual axis which connects a fovea and the fixation target (fixation point). In order to obtain the internal refractive power distribution from respective measurement data on corneal refractive power distribution and whole refractive power distribution, it is necessary to use the same positional reference. In the measurement apparatus 10 consistent with the present embodiment, the corneal shape measurement (corneal refractive power distribution measurement) and the eye refractive power distribution measurement (whole refractive power distribution measurement) are performed by using the same corneal reflex, so that the respective measurement data is obtained with respect to the same reference axis (i.e., the measurement optical axis L1=the visual axis). Besides, some wavefront aberration measurement apparatuses perform measurement with respect to the line of sight as the reference axis; therefore in such a case, either of the data is subjected to a coordinate conversion and corrected so that the respective data is obtained with respect to the same reference axis. Both of the wavefront aberration measurement apparatus and the processor 101 may answer the purpose of making this correction.

Figure 4A:
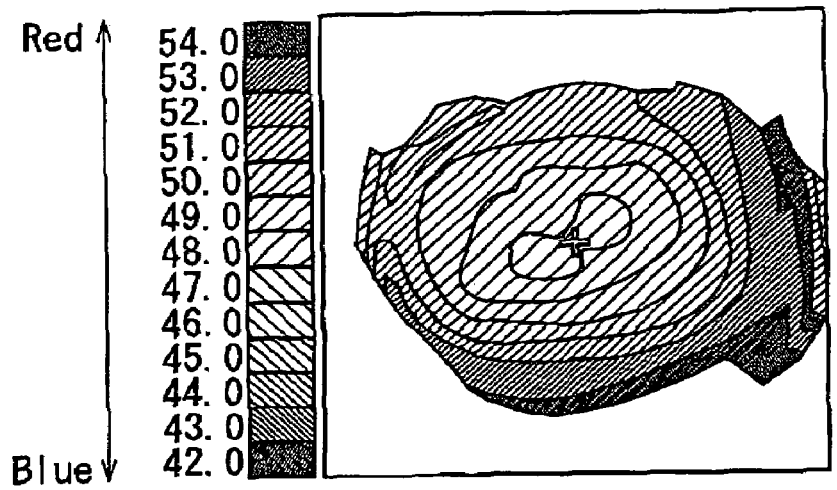
FIGS. 4A, 4B and 4C are examples of displaying corneal refractive power distribution, whole refractive power distribution and internal refractive power distribution of a normal eye in color-scaled maps.
Figure 4B:
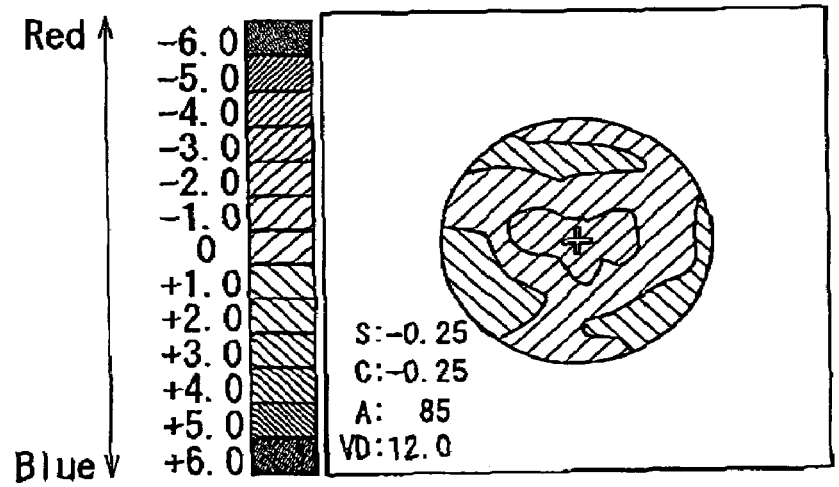

A method for calculating the internal refractive power distribution will be described. The corneal curvature distribution obtained by the corneal shape measurement may be represented as corneal refractive power distribution. The corneal refractive power here is refractive power obtained based on a distance of light from an infinite distance, between an arbitrary point on the corneal surface where the entering light is refracted and a point on the measurement optical axis where the refracted light meets the axis. In this case, the Snell's law is applied with respect to the arbitrary point on the corneal surface. On the other hand, obtained by eye refractive power distribution measurement is whole refractive power distribution of an eye. The whole refractive power referred to herein is obtained by regarding a distance from an arbitrary point on the measurement optical axis to a retina as a refractive power error, at which point light from an infinite distance entering an eye at an arbitrary point on the corneal surface meets the measurement optical axis. The corneal refractive power distribution and the whole refractive power distribution are obtained respectively as refractive power distribution since both of them are calculated with respect to the light entering at the arbitrary points on the cornea. Results thereof are displayed on the display 102 as color-scaled maps as shown in FIGS. 4A and 4B. FIG. 4A is an example of displaying the corneal refractive power distribution in a color-scaled map, and FIG. 4B is an example of displaying the whole refractive power distribution in a color-scaled map.

Figure 4C:
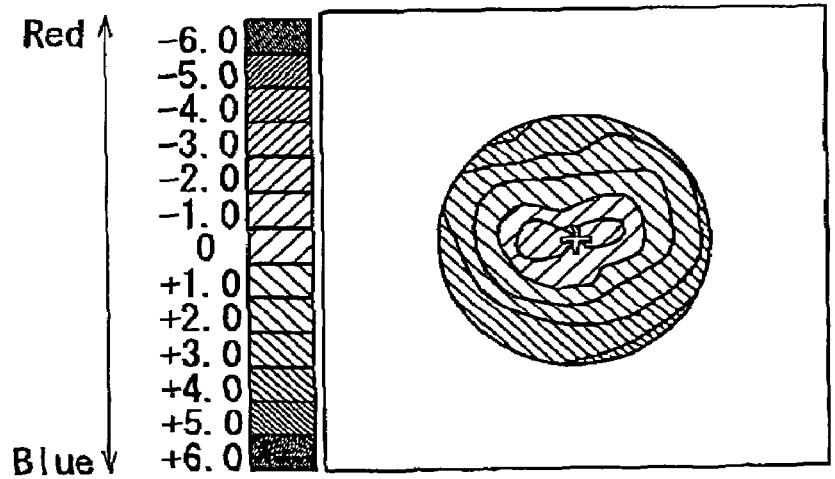

Here, the whole refractive power distribution is represented generally as refractive power of correctives for refractive power, such as spectacles and contact lenses (i.e., a refractive power error with respect to an emmetropia), which is different from corneal refractive power. For example, assuming that an eye with the corneal refractive power of 43D is an emmetropia with the whole refractive power of 0D, an eye having the same axial length and with the corneal refractive power of 46D becomes a myopia with the whole refractive power of −3D. Since the whole refractive power is obtained by adding the corneal refractive power to the internal refractive power (i.e., the corneal refractive power+the internal refractive power=the whole refractive power), the internal refractive power is obtained by subtracting the corneal refractive power from the whole refractive power (i.e., the internal refractive power=the whole refractive power−the corneal refractive power). However, obtaining the internal refractive power using this expression brings about difficulties in understanding because its value becomes at the same level as that of the corneal refractive power. Therefore, only an astigmatic component and an irregular component excluding specific refractive power are obtained to be displayed in a color-scaled map. FIG. 4C is an example of displaying the internal refractive power distribution in a color-scaled map at this time. By setting the refractive power of the center portion of the eye in the color-scaled map showing the internal refractive power distribution as reference power=0D, the color-scaled map may be visually judged easily on a color scale whether a spherical aberration being a change in the refractive power in the peripheral portion is positive or negative. For example, green is imparted to the refractive power of the center portion of the eye (the reference power=0D), and the color varies gradually from green to blue as the positive refractive power becomes stronger, and varies gradually from green to red as the negative refractive power becomes stronger. Thus, in the internal refractive power distribution, by setting the refractive power of the center portion of the eye as the reference power=0D, the degree of the spherical aberration and whether the refractive power is positive or negative may be grasped easily.

Incidentally, while the corneal refractive power, the whole refractive power and the internal refractive power are all refractive power, a reference position is previously defined when treating a relationship among them. For example, by defining a corneal vertex on the visual axis (being a point on the corneal surface through which the measurement optical axis=the visual axis passes, in the measurement apparatus 10 of the present embodiment) as the reference position, the understanding of an ophthalmologist is facilitated. Besides, in the display examples of the color-scaled maps of FIGS. 4A, 4B and 4C, the reference position in the center portion of the eye is set at a position of the measurement optical axis which is the reference axis for calculating the internal refractive power distribution.

The processor 101 obtains the internal refractive power distribution from the above-mentioned relationship to display in a color-scaled map. Owing to the color-scaled map display, in the case of a normal eye, the internal refractive power distribution can be estimated to show refractive power distribution of a crystalline lens. FIGS. 4A, 4B and 4C are the display examples of the color-scaled maps in the case of the normal eye, where the internal refractive power distribution is formed concentrically (see FIG. 4C). In the case of an eye where an intraocular lens is implanted, the internal refractive power distribution can be estimated to show refractive power distribution of the intraocular lens. However, in the case of the eye where the intraocular lens is implanted in a slanting position, the internal refractive power distribution contains a component of the slant. In addition, in the case of an eye with keratoconus or with an irregular cornea, the internal refractive power distribution contains an influence of its corneal posterior surface.

Figure 5A:
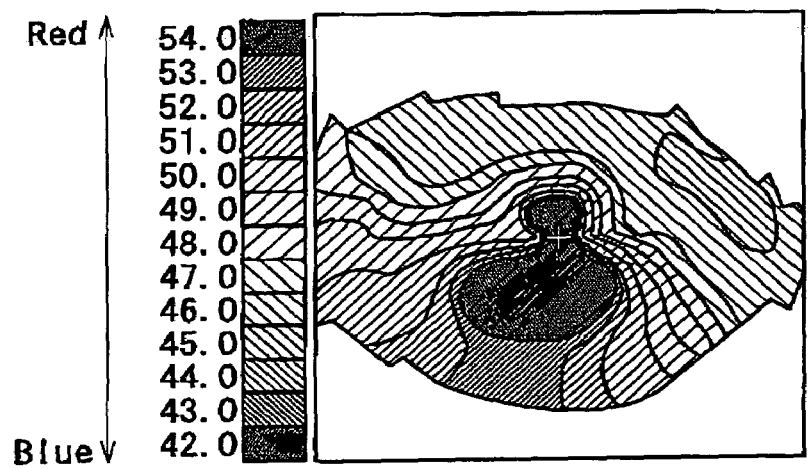
FIGS. 5A, 5B and 5C are examples of displaying corneal refractive power distribution, whole refractive power distribution and internal refractive power distribution of an eye with keratoconus in color-scaled maps.
Figure 5B:
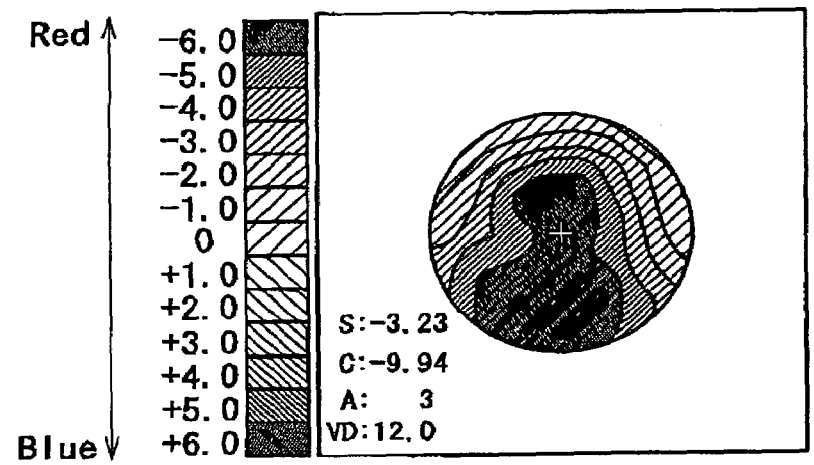
Figure 5C:
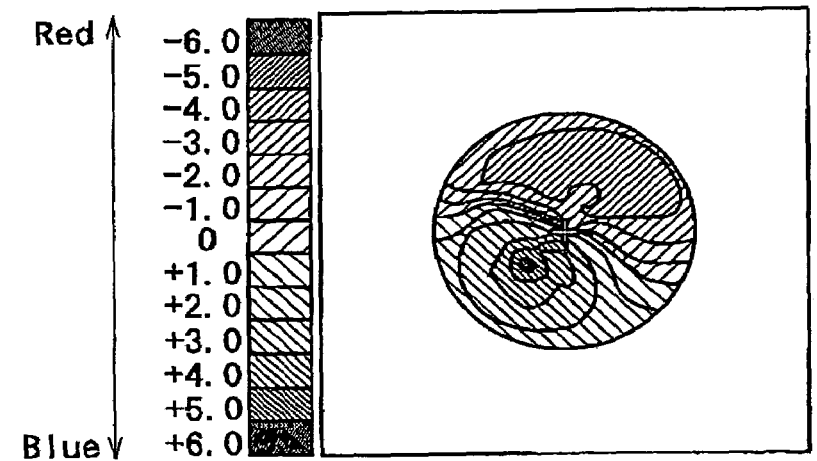

FIGS. 5A, 5B and 5C are display examples of color-scaled maps in the case of the eye with keratoconus. FIG. 5A is the example of displaying the corneal refractive power distribution in a color-scaled map, FIG. 5B is the one of displaying the whole refractive power distribution in a color-scaled map, and FIG. 5C is the one of displaying the internal refractive power distribution in a color-scaled map. In FIG. 5C, the internal refractive power distribution is not formed concentrically as shown in FIG. 4C, and a color showing the refractive power changes sequentially toward both ends of a display area. That is to say, this internal refractive power distribution contains a prism component. Also in the case of the eye where the intraocular lens is implanted, a color-scaled map showing the internal refractive power distribution when the intraocular lens is slanted becomes like the one where the color showing the refractive power changes sequentially toward the both ends as shown in FIG. 5C.

Such a color-scaled map serves its purpose in a case where the internal refractive power is considered as refractive power between the corneal posterior surface and the retina since the color-scaled map is viewed as representing the influence of the corneal posterior surface or the slant of the intraocular lens in the eye. However, the prism component interferes with finding the refractive power distribution of the crystalline lens of the human eye and of the intraocular lens. This is because, in general, the refractive power distribution of the crystalline lens is formed concentrically or elliptically about the visual axis (optical axis), and the refractive power distribution of the intraocular lens is formed concentrically (as a spherical/aspherical lens) about the visual axis (optical axis). There are primarily various factors which contribute to generation of the prism component as described above: for example, the factor that an eye is an asymmetric optical system; the factor that a cornea includes asymmetric astigmatism; the factor that a cornea includes pathologic deformation like keratoconus; the factor that an axis of an eye is deviated at the time of corneal refractive surgery; and the factor that an intraocular lens is implanted in an eye in a slanting position.

Figure 6:
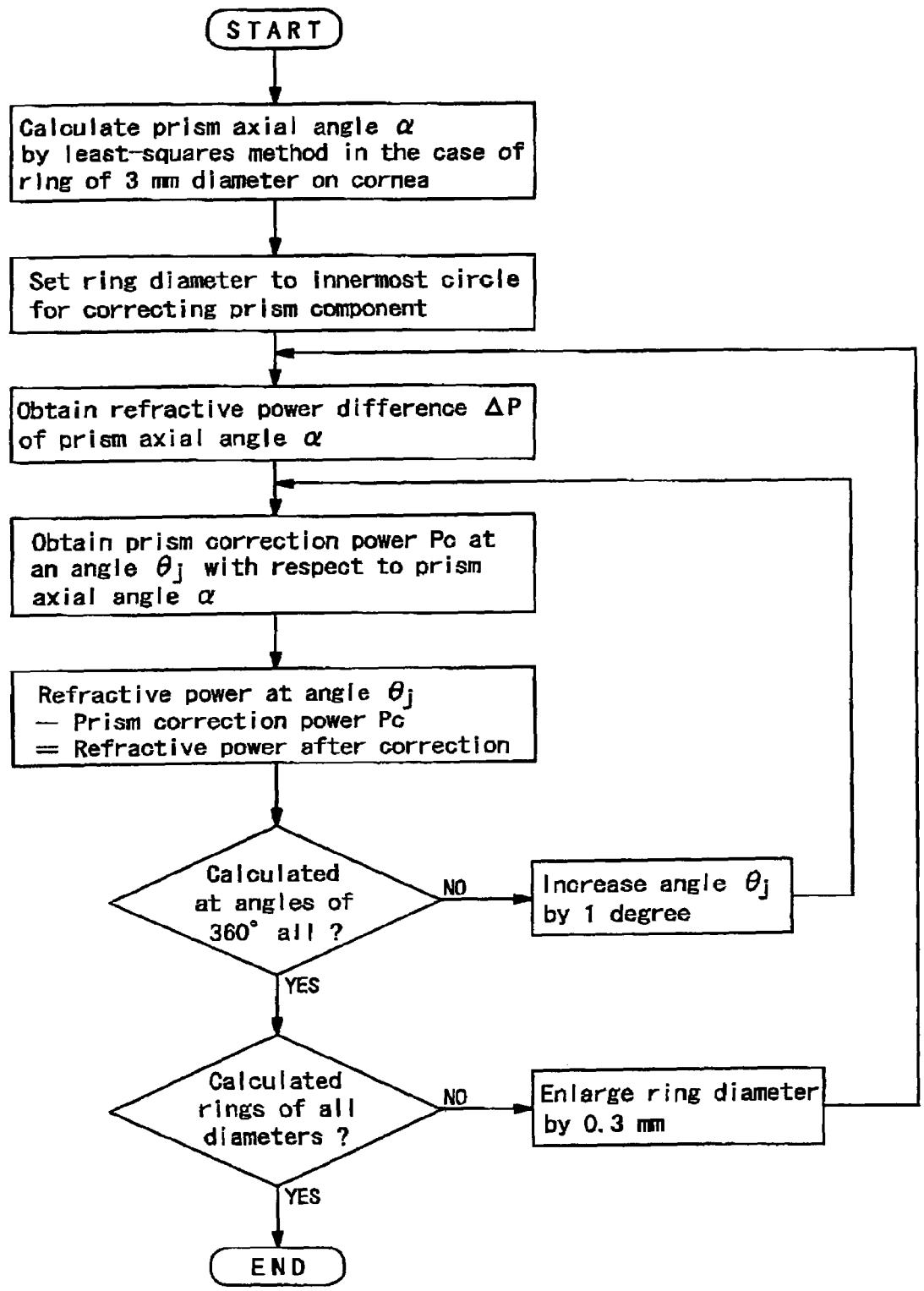
FIG. 6 is a flowchart showing a method for removing a prism component from internal refractive power distribution.

Hereinafter, a method for removing the prism component (slant component) from the internal refractive power distribution will be described (see a flowchart shown in FIG. 6) Besides, as the data on the internal refractive power distribution is calculated from the data on the corneal refractive power distribution and the whole refractive power distribution, the respective data on the corneal refractive power distribution and the whole refractive power distribution is subjected to pre-processing for making the data into more high-density ring-shaped one by complementing sampling-intervals in a direction of the radius to bring the respective data into correspondence with each other. For example, the ring-shaped data in the direction of the radius is to be obtained in respect of rings of 0.9 mm to 6.0 mm diameters in steps of 0.3 mm.

In data on the internal refractive power distribution in a ring of an arbitrary diameter having the reference axis L1 of the refractive power distribution as its center, for example, in data on the internal refractive power distribution in the ring of 3 mm diameter on a cornea which corresponds to a region that matters to visual acuity, an axial angle of the prism component (i.e., a base-direction of a prism, and hereinafter, it is referred to as a prism axial angle) which is generated with respect to the reference axis L1 is obtained by the least-squares method. The least-squares method is expressed as follows. As an expression giving general data on a circumference of a prism, the expression 1 is considered.

$$A + B \cdot \cos(\alpha + \theta_i) \qquad \text{[Expression 1]}$$

Here, A represents an offset amount, B represents prism power, $\alpha$ represents a prism axial angle, $\theta_i$ represents a meridian angle (i=0, 1, 2, 3, . . . 359). In addition, refractive power at an arbitrary meridian angle is set to be $d_i$ (i=0, 1, 2, 3, . . . 359). Based on a definition of the least-squares method, taking account of a difference from $d_i$, the respective coefficients are obtained so that a solution to the following expression 2 is minimized.

$$\sum_{i=0}^{N} (A + B \cdot \cos(\alpha + \theta_i) - d_i)^2 \qquad \text{[Expression 2]}$$

In order to have the solution to the expression 2 minimized, respective solutions to an expression where the expression 2 is partially differentiated with respect to the coefficient A, an expression where the expression 2 is partially differentiated with respect to the coefficient B, and an expression where the expression 2 is partially differentiated with respect to $\alpha$, are obtained so as to be zero. Solving these expressions allows $\alpha$ to be obtained by the following expression 3.

$$\tan(\alpha) = \frac{\sum_{i=0}^{n} \sin(\theta_i) \cdot d_i}{\sum_{i=0}^{n} \cos(\theta_i) \cdot d_i} \qquad \text{[Expression 3]}$$

Figure 7:
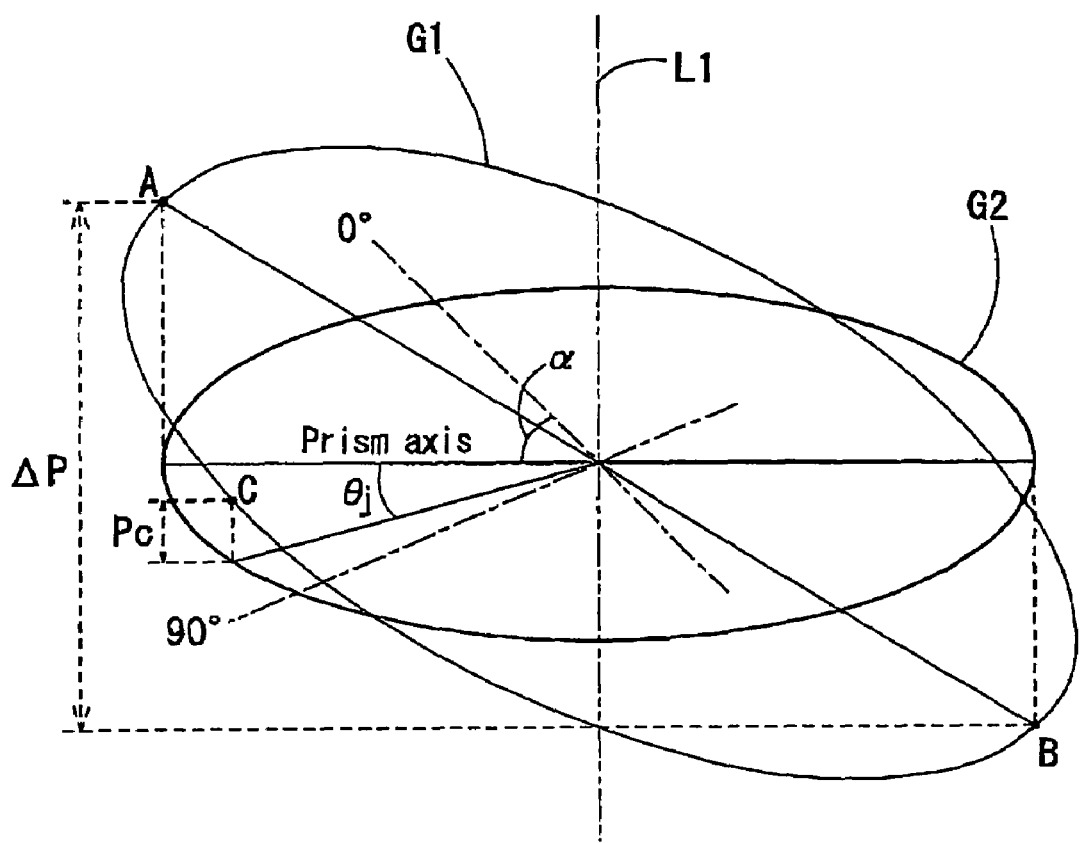
FIG. 7 is a view illustrating correction (removal) of the prism component.

After $\alpha$ (the prism axial angle) which indicates a direction for correcting the prism component is determined, a correction prism power at an angle $\theta_j$ with respect to the prism axial angle α (prism axis) is calculated with respect to the data on the internal refractive power distribution in the rings of the respective diameters (i.e., the data in the rings of 0.9 mm to 6.0 mm diameters in steps of 0.3 mm). This calculation is described referring to FIG. 7. In FIG. 7, a figure G1 represents the data on the refractive power distribution in a ring of a specific diameter having the reference axis L1 as its center where the prism component is yet to be removed from the data, and a figure G2 represents the data on the refractive power distribution in a ring of the same specific diameter where the prism component is removed from the data. The figure G1 (the ring data where the prism component is yet to be removed) is illustrated three-dimensionally as being in a slanting position with respect to the figure G2 (the ring data where the prism component is removed). Concerning the refractive power distribution with respect to the reference axis L1, the maximum refractive power difference of the prism axial angle α is obtained as a difference ΔP between refractive power P(α) at an A point in the α direction and refractive power P(α+180) at a B point which is on the other side by 180° in the figure G1. In FIG. 7, a correction prism power Pc at a C point at the angle $\theta_j$ with respect to the prism axial angle α, is expressed as:

$$Pc=(\Delta P/2) \times \cos(\theta_j).$$

In this expression, the angle $\theta_j$ is varied from 0 to 359° to obtain the correction prism power $Pc(\theta_j)$ sequentially every angle. Subtracting the correction prism power $Pc(\theta_j)$ from the refractive power $P(\theta_j)$ in the respective meridian directions ($\theta_j$) gives refractive power at the respective positions after correction. After the prism axial angle α is determined, the calculation program sets a diameter of a ring (0.9 mm to 6.0 mm in steps of 0.3 mm) to be that of the innermost circle for obtaining the refractive power distribution, and sequentially enlarges the ring diameter. In the present embodiment, the calculation is performed with respect to 18 rings in total; and thereby the refractive power distribution where the prism component is removed (i.e., the corrected refractive power distribution) is obtained.

Figure 8:
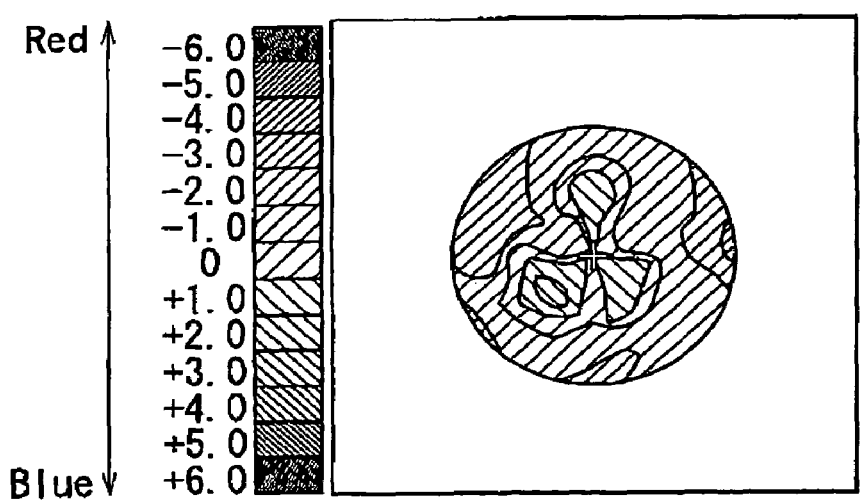
FIG. 8 is an example of displaying internal refractive power distribution in a color-scaled map, which is obtained by removing the prism component from the internal refractive power distribution shown in FIG. 5c.

FIG. 8 is an example displaying the internal refractive power distribution in a color-scaled map which is obtained by removing the prism component from the internal refractive power distribution shown in FIG. 5C. In this example, the prism component being removed, the displayed internal refractive power distribution is relatively close to a concentric circle.

Above-described achievement of the estimation of the internal refractive power distribution where the prism component is removed allows a wider range of diagnosis. That is to say, in the eye with keratoconus or the eye having its axis deviated at the time of corneal refractive surgery, since removing an influence of the prism component from the corneal surface and the corneal posterior surface allows estimation of the refractive power distribution of the crystalline lens, the estimated refractive power distribution may be exploited, for example, by being observed over time, in researches into a mechanism of progression of presbyopia, localization of a region where cataract develops, and the like. In addition, in the eye where the intraocular lens (including an intraocular contact lens) is implanted, an optical type of the implanted intraocular lens (such as a spherical lens, an aspherical lens, a lens for astigmatism, and a multifocal lens) may be specified since true refractive power distribution obtained by removing the slant may be estimated; and thereby re-surgery to implant a more appropriate lens for reducing an eye aberration and the like may be planned. In addition, though distortion due to a loop pressure in the case of a foldable intraocular lens gives rise to an eye aberration, a judgment on the presence of such an eye aberration may be formed, allowing the judgment to be reflected on design of a material, a shape and the like of the intraocular lens.

Incidentally, in the case of displaying only the internal refractive power distribution in a color-scaled map where the prism component is removed, information about the influence of the corneal surface, the slant of the intraocular lens and the like are lost unintentionally. In diagnosis, various points of view also count. The presence of the prism component in the internal refractive power distribution suggests a slant of the corneal posterior surface or the slant of the intraocular lens, which itself has clinical significance. Therefore, it is preferable for an ophthalmologist to select between correcting (removing) and not correcting (not removing) the above-described prism component. This selection is implemented by inputting a selecting signal on a setting screen displayed on the display 102 by the use of the input device 103. The selection between correcting (removing) and not correcting (not removing) the prism component encompasses the selection between displaying and not displaying the corrected color-scaled map.

Besides, the above-described preferred embodiment is one example, and not intended to limit the invention to this. The prism axial angle α is obtained by the least-squares method in the present embodiment, however, it may be obtained by the first term of Fourier Transform, or by Zernike's polynomials. In addition, the ring of about 3 mm diameter is used in obtaining the prism axial angle α in the present embodiment, however, the diameter may be designated arbitrarily to be 2.5 mm, 4.0 mm or the like. In this case, the diameter is designated on the setting screen displayed on the display 102 by the use of the input device 103. Further, the prism axial angle α may be determined by averaging a plurality of axial angles which are obtained from rings of varying diameters, or by the least-squares method using the obtained angles.

In addition, as for the data on the whole refractive power distribution for calculating the internal refractive power distribution, such data may also be used that is obtained by converting data on the wavefront aberration which is obtained by the wavefront aberration measurement apparatus into the data on the whole refractive power distribution. Since the refractive power distribution and the wavefront aberration have a reversible relationship, inputting the data on the whole refractive power distribution encompasses inputting and converting the data on the wavefront aberration. Also as for inputting the data on the corneal refractive power distribution for calculating the internal refractive power distribution, it encompasses inputting data on the corneal curvature distribution being the result of the corneal shape measurement and converting it into the data on the corneal refractive power distribution.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
an input unit which inputs measurement data on both a corneal refractive power distribution of an eye of an examinee and a whole refractive power distribution of the eye, the refractive power distributions both being with respect to a same reference axis; and
a calculation unit which:
obtains with respect to the same reference axis an internal refractive power distribution that is a refractive power distribution between a corneal posterior surface and a retina of the eye based on the measurement data on both the corneal refractive power distribution and the whole refractive power distribution, and
removes a prism component from the internal refractive power distribution.

2. The ophthalmic apparatus according to claim 1, wherein the calculation unit:
obtains an axial angle of the prism component with respect to the same reference axis,
obtains prism components in plural rings of different diameters having the same reference axis as its center at the axial angle, and
removes the prism components in plural rings from the internal refractive power distribution.

3. The ophthalmic apparatus according to claim 1, further comprising a display unit which displays in a color-scaled map at least one of the internal refractive power distribution where the prism component is yet to be removed and an internal refractive power distribution where the prism component is removed.

4. A method of calculating an internal refractive power distribution that is a refractive power distribution between a corneal posterior surface and a retina of an eye of an examinee, comprising the steps of:
inputting measurement data on both a corneal refractive power distribution of the eye and a whole refractive power distribution of the eye, the refractive power distributions both being with respect to a same reference axis;
obtaining with respect to the same reference axis the internal refractive power distribution based on the measurement data on both the corneal refractive power distribution and the whole refractive power distribution; and
removing a prism component from the internal refractive power distribution.

5. The method of calculating the internal refractive power distribution according to claim 4, comprising the steps of:
obtaining an axial angle of the prism component with respect to the same reference axis;
obtaining prism components in plural rings of different diameters having the same reference axis as its center at the axial angle; and
removing the prism components in plural rings from the internal refractive power distribution.

* * * * *